United States Patent [19]

Verhoeven et al.

[11] Patent Number: 5,672,638
[45] Date of Patent: Sep. 30, 1997

[54] BIOCOMPATABILITY FOR SOLID SURFACES

[75] Inventors: Michel Verhoeven, Maastricht; Linda L. Cahalan, Geleen; Marc Hendriks, Hoensbroek; Benedicte Fouache, Maastricht; Patrick T. Cahalan, Geleen, all of Netherlands

[73] Assignee: Medtronic, Inc., Minneapolis, Minn.

[21] Appl. No.: 517,788

[22] Filed: Aug. 22, 1995

[51] Int. Cl.[6] .................. A61F 2/02; C12N 11/08
[52] U.S. Cl. .................. 523/112; 523/113; 424/423; 424/78.36; 435/180; 435/181; 427/2.25; 623/1
[58] Field of Search .................. 424/423, 78.36; 435/180, 181; 523/112, 113; 623/1; 427/2.25

[56] References Cited

U.S. PATENT DOCUMENTS

| | | | |
|---|---|---|---|
| 3,826,678 | 7/1974 | Hoffman et al. | 117/81 |
| 4,118,485 | 10/1978 | Eriksson et al. | 424/183 |
| 4,378,435 | 3/1983 | Takagi et al. | 435/180 |
| 4,521,564 | 6/1985 | Solomon | 525/54.1 |
| 4,526,714 | 7/1985 | Feijen et al. | 260/112 R |
| 4,565,740 | 1/1986 | Golander et al. | 428/409 |
| 4,600,652 | 7/1986 | Solomon et al. | 428/423.3 |
| 4,613,665 | 9/1986 | Larm | 536/20 |
| 4,634,762 | 1/1987 | Feijen et al. | 530/350 |
| 4,642,242 | 2/1987 | Solomon et al. | 427/2 |
| 4,720,512 | 1/1988 | Hu et al. | 523/112 |
| 4,749,653 | 6/1988 | Lee et al. | 435/176 |
| 4,786,556 | 11/1988 | Hu et al. | 428/412 |
| 5,032,666 | 7/1991 | Hu et al. | 528/70 |
| 5,049,403 | 9/1991 | Larm et al. | 427/2 |
| 5,077,372 | 12/1991 | Hu et al. | 528/70 |
| 5,132,108 | 7/1992 | Narayanan et al. | 424/78.17 |
| 5,229,172 | 7/1993 | Cahalan et al. | 427/536 |
| 5,278,200 | 1/1994 | Coury et al. | 523/112 |
| 5,308,641 | 5/1994 | Cahalan et al. | 427/2 |
| 5,344,455 | 9/1994 | Keogh et al. | 623/11 |
| 5,350,800 | 9/1994 | Verhoeven et al. | 525/54.2 |
| 5,415,938 | 5/1995 | Cahalan et al. | 428/409 |

FOREIGN PATENT DOCUMENTS

| | | |
|---|---|---|
| 0186523 | 7/1986 | European Pat. Off. |
| 1310007 | 5/1973 | United Kingdom. |
| 2023022 | 12/1979 | United Kingdom. |

Primary Examiner—Andrew E. C. Merriam
Attorney, Agent, or Firm—Daniel W. Latham; Harold R. Patton

[57] ABSTRACT

An improved coating and spacer material for a medical device having a blood or tissue-contacting surface comprising a polyalkyleneimine layer which is crosslinked with a crosslinking agent which is at least difunctional in polymerizable vinyl groups which have adjacent strong electron-withdrawing groups and a biomolecule covalently bonded to the crosslinked polyalkyleneimine layer. For example, polyethyleneimine crosslinked with divinyl sulfone could be used. The resulting crosslinked spacer layer has improved uniformity and stability without materially limiting the covalent attachment of a biomolecule such as heparin.

6 Claims, No Drawings

BIOCOMPATABILITY FOR SOLID SURFACES

BACKGROUND OF THE INVENTION

This invention relates to the enhancement of the biocompatability of various surfaces of medical devices by binding biomolecules such as heparin to the surface.

Medical devices which serve as substitute blood vessels, synthetic and intraocular lenses, electrodes, catheters and the like in and on the body or as extracorporeal devices intended to be connected to the body to assist in surgery or dialysis are well known. However, the use of such biomaterials in medical devices can stimulate adverse body responses, including rapid thrombogenic action. Various plasma proteins play a role in initiating platelet and fibrin deposition on plastic surfaces. These actions lead to vascular constriction to hinder blood flow, and the inflammatory reaction that follows can lead to the loss of function of the medical device.

A "biomaterial" may be defined as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; will substantially maintain its physical properties and function during the time that it remains implanted in or in contact with the body As used herein, the solid surface of a biomaterial is characterized as "biocompatible" if it is capable of functioning or existing in contact with biological fluid and/or tissue of a living organism with a net beneficial effect on the living organism. Long term biocompatibility is desired for the purpose of reducing disturbance of the host organism. One approach to improved biocompatibility for biomaterials is to attach various "biomolecules" which can promote the thromboresistance of the device. Immobilization of polysaccharides such as heparin to biomaterials has been researched extensively to improve bio- and hemocompatibility. The mechanism responsible for reduced thrombogenicity of heparinized materials is believed to reside in the ability of heparin to speed up the inactivation of serine proteases (blood coagulation enzymes) by AT-III. In the process, AT-III forms a complex with a well defined pentasaccharide sequence in heparin, undergoing a conformational change and thus enhancing the ability of AT-III to form a covalent bond with the active sites of serine proteases such as thrombin. The formed TAT-complex then releases from the polysaccharide, leaving the heparin molecule behind for a second round of inactivation.

Usually, covalent immobilization of heparin to a biomaterial consists of activating the material in such a way that coupling between the biomaterial and functional groups on the heparin (—COOH, —OH, —NH$_2$) can be achieved. Thromboresistant surfaces are not necessarily obtained using these processes. Heparin can be bound too tightly to the surface due to the high abundance of functional groups on the heparin, or coupling may result from bonds between the active pentasaccharide sequence on the heparin and the biomaterial, preventing activation of AT-III and thus catalytic deactivation of the proteases. In order to obtain truly anti-thrombogenic surfaces, proper immobilization of the biomolecules is key. Larm presented (in U.S. Pat. No. 4,613,665) a method to activate heparin via a controlled nitrous acid degradation step, resulting in degraded heparin molecules of which a part containing a free terminal aldehyde group. Heparin in this form can be covalently bound to an aminated surface in a reductive amination process. Although the molecule is degraded and as a result shows less catalytic activity in solution, the end point attachment of this type of heparin to a surface results in true anti-thromogenicity due to the proper presentation of the biomolecule to the surface. In this fashion, the molecule is freely interacting with AT-III and the coagulation enzymes, preventing the generation of thrombi and microemboli.

Besides the coupling of heparin via its natural functional groups or through a terminal aldehyde group, coupling of heparin via aldehyde groups randomly introduced into the chain by means of periodate oxidation has also been described. Solomon et al (in U.S. Pat. Nos. 4,600,652 and 4,642,242) and Hu et al (in U.S. Pat. Nos. 4,720,512; 4,786,556; 5,032,666 and 5,077,372) coupled heparin after periodate oxidation to an amated polyurethane obtaining a material with high loading of stably bound heparin.

Spacer molecules have been used to connect heparin and other biomolecules to a substrate. A spacer molecule is a molecule or compound which is capable of attachment to a solid surface, is large enough to extend from the surface of said surface and is capable of mobilizing a biomolecule and/or biomolecules. The spacer insures that the active site of the biomolecule is held outward away from the support so as to contact the body fluid efficiently. The spacers are derived from organic molecules having at least two reactive functional groups generally situated at opposing ends of the molecule. Such groups serve as attachment vehicles capable of coupling the spacer to the solid surface and to the biomolecule. For example, in U.S. Pat. No. 5,132,108 to Narayanan et al., a copolymer surface was subjected to radiofrequency plasma treatment by subjecting it to a radiofrequency electric field in the presence of a water vapor plasma medium. An aqueous solution of polyethyleneimine (PEI) and 1-(3-dimethylaminopropyl)-3-ethylcarbodiimide (EDC) coupling agent was applied to the radiofrequency plasma discharge modified polyurethane surface. An aqueous solution of heparin and EDC was then applied to the PEI-treated surface in order to provide a polymeric surface having an anti-thrombogenic agent secured to its surface. However, the addition of such spacer molecules to implanted medical device surfaces also adds instability to the surfaces and increases the prospect for burial of the attached biomolecule in the spacer layer and also for damage to the surfaces as the device is handled or implanted.

Additional stability can be provided, for example, according to U.S. Pat. No. 4,565,740 to Colander et al. or U.S. Pat. No. 5,049,403 to Larm et al. In the first of these patents, a complex of a polymeric cationic surfactant (e.g. polyethyleneimine) and a dialdehyde (e.g. glutaraldehyde) is adsorbed onto a substrate material. In the second of these patents, a polyamine is adsorbed onto the surface of a substrate and crosslinked with crotonaldehyde. However, glutaraldehyde and crotonaldehyde do not provide a stable crosslink immediately since the bonds formed are of the hydrolytically unstable imine type. As a consequence, relatively high levels of crosslinkers are used which might cause excessive crosslinking and even precipitation as the crosslinking proceeds. This leads to irregular coating. Furthermore, due to the high level of crosslinker needed to obtain effective crosslinking, the crosslinkers are not used in the top layer of polyamine in order not to compromise the level of primary and secondary amines needed for immobilization of the biomolecule.

It is therefore an object of the invention to provide a medical device surface for the attachment of heparin and other biomolecules with a crosslinked spacer layer of improved uniformity.

It is also an object of the invention to provide a spacer in which the portion of the spacer nearest to the biomolecule is crosslinked and thereby provides a spacer of improved stability.

SUMMARY OF THE INVENTION

We have discovered an improved coating and spacer material for a medical device having a blood or tissue-contacting surface and a method for making it comprising a polyalkyleneimine layer which is crosslinked with a crosslinking agent which is at least difunctional in polymerizable vinyl groups which have adjacent strong electron-withdrawing groups and a biomolecule covalently bonded to the crosslinked polyalkyleneimine layer. The polyalkyleneimine can be, for example, polyethyleneimine and the crosslinking agent can be, for example, divinyl sulfone. This spacer material and coating can be made by reacting the polyalkyleneimine with the crosslinking agent, applying the reacted composition to the solid surface and then bonding the biomolecule to the amine functionalities of the crosslinked polyalkyleneimine coating. When the biomolecule is heparin, the heparin can be attached to the amine functionalities by treating the heparin to produce a pendant aldehyde group on the heparin and then bringing the heparin into contact with the crosslinked polyalkyleneimine. The amount of the crossing agent used in making the spacer material is small enough to leave an adequate population of amine groups in the spacer material to bond to the biomolecule. For example, when using divinyl sulfone as the crosslinker for polyethyeleneimine (i.e. having 12 mmol per gram total amines with a ratio of primary amine:secondary amine:tertiary amine or 1:2:1), only about 50–1000 micromol of crosslinker should be used per gram of polyethyleneimine with preferably 100–200 micromol of crosslinker used per gram of polyethyleneimine. Preferably, the crosslinking agent used to crosslink the polyalkyleneimine is reacted with the polyalkyleneimine in dilute aqueous solution and at a suitable pH to accomplish the light crosslinking of the polyalkyleneimine.

DETAILED DESCRIPTION OF THE INVENTION

In the present method, a medical device can be provided with a blood or tissue-compatible surface of improved biocompatibility. By medical device, is meant devices which have surfaces which contact blood or tissue of a patient in the course of their operation. This can include, for example, extracorporeal devices for use in surgery such as blood oxygenators, blood pumps, blood sensors, tubing used to carry blood and the like which contact blood which is then returned to the patient. This can also include endoprostheses implanted in blood or tissue contact in a human or animal body such as vascular grafts, stents, pacemaker leads, heart valves and the like which are implanted in blood vessels or in the heart. This can also include devices for temporary intravascular use such as catheters, guide wires and the like which are placed into the blood vessels or the heart for purposes of monitoring or repair.

In the present invention, a polyalkyleneimine reacted with a crosslinking agent which is at least difunctional in vinyl groups is applied to a solid surface and is employed to provide a spacer on the solid surface for the purpose of improving its biocompatibility. The solid surface that is rendered biocompatible is desirably of a synthetic or natural material that is insoluble in physiological fluids. The surface may be one or more surfaces of devices intended to function in contact with tissue and/or fluids of living organisms. The substrate for this solid surface of the device may be any suitable metal such as titanium, tantalum or stainless steel or a polymer such as polyurethane, polyvinylpyrrolidone, silicone elastomers, polyolefins such as polyethylene or polypropylene, polytetrafluoroethylene, polyvinyl chloride, polyesters, fluoropolymers, polyacrylates (including polymethacrylates); minerals or ceramics such as hydroxyapatite; human or animal tissue such as bone, skin and teeth; organic materials such as wood, cellulose and compressed carbon; and other natural and synthetic materials such as glass, rubber, wood and the like.

The polyamine used in the present invention can be, for example, polyethyleneimine or other branched polyalkyleneimines. By polyalkyleneimine, we mean to include the water soluble, hydrophilic, polyamines evolving from aziridine and azetidine monomers such as 1-unsubstituted imines, 1-substituted basic imines, activated imines (1-acyl substituted imines), isomeric oxazolines/oxazines and the like. The polyalkyleneimines employed in the present invention are preferably highly branched, thereby possessing primary, secondary, and tertiary amine groups. Thus, ethyleneimine polymerized by classical cationic chain-growth polymerization, either alone or with other monomers suitable for copolymerization with ethyleneimine, could be used in the present invention. The crosslinking agent employed in the present invention can be any crosslinking agent which is at least difunctional in vinyl groups and which includes adjacent to each of the vinyl groups strong electron-withdrawing groups which polarize the double bond of the vinyl group and make it susceptible to anionic attack. For example, sulfone, carbonyl, azo, sulfamido and nitro groups are strong electron-withdrawing groups which could be used. Divinyl compounds with adjacent sulfone groups are preferred such as compounds having the structure

where A is selected from the group consisting of

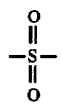

and

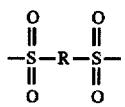

where R is a $C_1$ to $C_{10}$ alkyl group. The most preferred crosslinking agent is divinyl sulfone.

The spacer material of the present invention can therefore be made by reacting a polyalkyleneimine with the crosslinking agent and then applying the reacted mixture to the solid surface of the medical device. Preferably, the crosslinking agent used to crosslink the polyalkyleneimine is applied in dilute solution and in an amount and at a suitable pH to accomplish only light crosslinking and to preserve the amine functionality for the polyalkyleneimine surface that will allow biomolecules to readily bond to the spacer. This requires a stoichiometry for the reaction in which there is a substantial excess of amine groups. For example, when using divinyl sulfone as the crosslinker for polyethyeleneimine (i.e. a polyethyleneimine having 12 mmol per gram total amines with a ratio of primary amine:secondary amine-:tertiary amine or 1:2:1) , only about 50–1000 micromol of crosslinker should be used per gram of polyethyleneimine with preferably 100–200 micromol of crosslinker used per gram of polyethyleneimine. Thus, the amount of crosslinker reacted with the polyalkyleneimine should be limited so that a maximum of about ⅙ of the total amines could be used in the crosslinking reaction. Preferably, less than about ⅟₃₀ of the total amines would be used. The reaction between crosslinker and polyalkyleneimine preferably takes place in a dilute aqueous solution. For example, with polyethyleneimine as the polyalkyleneimine a concentration of polyethyleneimine of about 0.05 wt % could be used. Also, for example, a pH for the reaction solution in the range of about 7 to about 10 would be preferred for polyethyleneimine and divinyl sulfone. Since the reaction is limited by the relative stoichiometric excess of amine groups, no precise reaction time is required. The reaction between polyethyleneimine and divinyl sulfone in dilute solution can be allowed to proceed to completion at room temperature overnight.

The crosslinked polyalkyleneimine is preferably strongly bonded to the solid surface, for example, by covalently attaching the crosslinked polyalkyleneimine to the solid surface or an extension of the solid surface with an agent which has functional groups which react with the solid surface and the crosslinked polyalkyleneimine. For example, when the medical article has a polymeric surface, a thin but densely formed hydrogel graft polymer can be applied by providing a base layer of grafted acrylamide on the polymeric surface which can be used to attach the crosslinked polyalkyleneimine spacer. Such an acrylamide layer can be provided as set forth in our U.S. Pat. No. 5,229,172, which is incorporated herein by reference. Or, when the medical article has a metal or glass surface, the coating can include a silane compound having a vinyl functionality such that the silane adheres to the surface with the vinyl functionality pendant from the surface and then forming a graft polymer on the surface with applied silane such that the pendant vinyl functionality of the silane is incorporated into the graft polymer by covalently bonding it to the graft polymer. Or, alternatively, the crosslinked polyalkyleneimine can be the top layer (or also in the intermediate layers) in an ionically bonded complex as taught by U.S. Pat. No. 4,565,740 to Colander et al. or U.S. Pat. No. 5,049,403 to Larm et al.

The crosslinked polyalkyleneimine spacer of the present invention is used to attach heparin or other biomolecules to a solid surface. The biomolecule can be essentially any biomolecule which is attached to the solid surfaces of biomaterials to improve biocompatibility of the biomaterial. The biomolecule may be a growth factor such as endothelial cell growth factor, epithelial cell growth factor, osteoblast growth factor, fibroblast growth factor, platelet derived growth factor, neural growth factor, or angiogenic growth factor; an antimicrobial agent such as lysozyme or polymixin; an antithrombogenic agent such as heparin, fractionated heparins (e.g., on an AT-III column), heparan, heparan sulfate, chondroitin sulfate, modified dextran, albumin, streptokinase, tissue plasminogen activator (TPA) or urokinase; cell attachment proteins such as fibronectin or laminin; a thrombogenic agent such as collagen or a hydrophilic polymer such as hyaluronic acid, chitosan or methyl cellulose, and other proteins, carbohydrates and fatty acids. In a preferred embodiment, the biomolecule is heparin which has been modified to include an aldehyde group which is capable of reacting with one of the amine groups of the crosslinked polyalkyleneimine to covalently bond the heparin to the spacer.

The following examples provide specific embodiments of the invention.

EXAMPLE 1

A piece of coiled tantalum wire was ultrasonically cleaned in 2% Micro-clean for 30 minutes followed by ultrasonic treatment in deionized water for 30 minutes. This last step was repeated after which the coil was rinsed in isopropanol and dried at 50° C. for 20 minutes.

The cleaned coil was swirled in a 2% solution of trichlorovinylsilane (Merck Darmstadt, FRG) in xylene for 60 seconds followed by rinsing for 60 seconds in xylene, 60 seconds in isopropanol, 60 seconds in water and finally in acetone. The coil was then allowed to air dry overnight.

The dried coil was then placed into a glass tube which was filled with 15 ml of an aqueous solution of 35 wt % of freshly distilled acrylic acid and 5 wt % acrylamide. To the 15 ml of monomer solution, 0.9 ml of a solution of ceric ammonium nitrate (0.1M) in nitric acid (0.1M) was added. Deaeration was performed for 3–5 minutes at about 18 mm Hg followed by ultrasonic treatment for 10 minutes and an additional incubation of 35–40 minutes, all at room temperature. The grafted samples were then rinsed 10 times with deionized water at 50° C. followed by an overnight incubation at 50° C. Samples taken showed a deep stain when soaked in toluidine blue solution.

An aqueous solution of polyethyleneimine (PEI) (Polymin from BASF Mw=60,000) at a concentration of 0.05 wt % PEI was prepared in a 0.1M borate buffer pH=9.2. 100 micromol of divinyl sulfone was added to the solution per 0.5 gram PEI and allowed to react overnight. The coil was then incubated in the crosslinked PEI solution for one hour while shaking. After rinsing with deionized water, water soluble carbodiimide (1-(3-dimethylaminopropyl)-3-ethylcarbodiimide. HCl) at a concentration of 0.05M was added. Coupling of the PEI spacer was allowed to proceed for one hour while shaking followed by rinsing with deionized water for 10 minutes.

Oxidized heparin was prepared by adding 0.165 mg $NaIO_4$/ml to 5 mg native heparin (Akzo)/ml 0.05M phosphate buffer (pH=6.88; 0.025M $K_2HPO_4$+ $NaH_2PO_4$*$2H_2O$). After overnight oxidation under the exclusion of light, the resulting heparin solution was diluted in 0.4M acetate pH=4.6 at a ratio of 1:20. 0.1 mg of $NaCNBH_3$/ml was added to the diluted heparin and the coil was incubated in this solution for 2 hours at 50° C. After rinsing with deionized water, 1M NaCl and water again to remove loosely bonded heparin, the coil was incubated with toluidine blue which provided an even lilac stain, indicating successful heparinization. An additional bioactivity test was also successfully performed to determine the ability of the heparinized surface to deactivate thrombin via activation of previously adsorbed antithrombin III.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A method for making a medical device having a solid surface for contacting blood or tissue of a patient, the solid surface having applied thereto an immobilized biomolecule by the steps of:
   (a) reacting a polyalkyleneimine with a crosslinking agent which is at least difunctional in polymerizable vinyl groups, each of said polymerizable vinyl groups adjacent a strong electron-withdrawing group, the polyalkyleneimine present in stoichiometric excess in the reaction mixture such that less than about 1/6 of the total amine groups in the polyalkyleneimine are used in the reaction;
   (b) applying the reacted polyalkyleneimine to the solid surface; and
   (c) applying a biomolecule having a pendant aldehyde group to the applied polyalkyleneimine such that the pendant aldehyde group of the biomolecule covalently bonds to an amine functionality of the crosslinked polyalkyleneimine.

2. The method according to claim 1 wherein the polyalkyleneimine is polyethyleneimine.

3. The method according to claim 1 or 2 wherein the reaction between polyalkyleneimine and crosslinking agent takes place at alkaline pH with a crosslinking agent having the structure $$CH_2{=}CH{-}A{-}CH{=}CH_2$$

where A is selected from the group consisting of

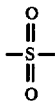

and

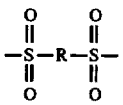

where R is a $C_1$ to $C_{10}$ alkyl group.

4. A method for making a medical device having a solid surface for contacting blood of a patient, the solid surface having applied thereto an immobilized heparin by the steps of:
   (a) reacting a polyalkyleneimine with a crosslinking agent which is at least difunctional in polymerizable vinyl groups, each of said polymerizable vinyl groups adjacent a strong electron-withdrawing group selected from the group consisting of sulfone, carbonyl, azo, sulfamido and nitro groups, the polyalkyleneimine present in stoichiometric excess in the reaction mixture such that less than about 1/6 of the total amine groups in the polyalkyleneimine are used in the reaction;
   (b) applying the reacted polyalkyleneimine to the solid surface;
   (c) treating heparin to produce a pendant aldehyde group on the heparin; and
   (d) applying a the treated heparin to the applied polyalkyleneimine such that the pendant aldehyde group of the
   (d) applying a the treated heparin to the applied polyalkyleneimine such that the pendant aldehyde group of the heparin covalently bonds to an amine functionality of the crosslinked polyalkyleneimine.

5. The method according to claim 4 wherein the reaction between polyalkyleneimine and crosslinking agent takes place at alkaline pH with a crosslinking agent having the structure $$CH_2{=}CH{-}A{-}CH{=}CH_2$$

where A is selected from the group consisting of

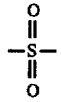

and

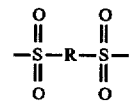

where R is a $C_1$ to $C_{10}$ alkyl group.

6. The method according to claim 1 or 4 wherein the polyalkyleneimine is present in the reaction mixture such that less than about 1/30 of the total amine groups in the polyalkyleneimine are used in the reaction.

* * * * *